US005254796A

United States Patent [19]

Dietz et al.

[11] Patent Number: 5,254,796

[45] Date of Patent: Oct. 19, 1993

[54] OXIDATION PROCESS

[75] Inventors: Erwin Dietz, Kelkheim; Siegfried Schiebler, Bad Soden am Taunus, both of Fed. Rep. of Germany

[73] Assignee: Hoechst Aktiengesellschaft, Frankfurt, Fed. Rep. of Germany

[21] Appl. No.: 899,726

[22] Filed: Jun. 17, 1992

[30] Foreign Application Priority Data

Jun. 18, 1991 [DE] Fed. Rep. of Germany ....... 4119996

[51] Int. Cl.[5] ...................... C07D 311/78; C07B 41/08

[52] U.S. Cl. .................................... 588/206; 549/232; 562/419; 562/541

[58] Field of Search ................ 549/232; 562/419, 541; 588/206; 423/429

[56] References Cited

U.S. PATENT DOCUMENTS 4,599,431 7/1966 Schiessler et al. .................. 549/232

*Primary Examiner*—Bernard Dentz

*Attorney, Agent, or Firm*—Connolly and Hutz

[57] ABSTRACT

The invention relates to an ecologically favorable process for the hydrolytic decomposition of halogen-containing compounds of the formula $CX_4$ or $CHX_3$ or mixtures of these compounds, in which X as halogen is chlorine or bromine or a combination thereof, in an aqueous-alkaline medium, which comprises first keeping the aqueous-alkaline reaction mixture comprising the abovementioned halogen-containing compounds at a temperature of between 0° and 1000° C. under the autogenous pressure which is formed in a closed reaction vessel for a period of up to 10 hours and then subjecting the mixture to a heat treatment at a temperature of between 70° and 150° C. under the autogenous pressure which is formed therein, in the presence of sulfite. The process according to the invention is particularly suitable for hydrolytic decomposition of halogen-containing reaction products from aqueous-alkaline hypohalite oxidations. The preparation of naphthalene-1,4,5,8-tetracarboxylic acid and its tetraalkali metal salts can be carried out in an ecologically particularly favorable manner by the process according to the invention.

20 Claims, No Drawings

OXIDATION PROCESS

DESCRIPTION

The present invention relates to an ecologically favorable oxidation process for organic compounds using hypohalites as oxidizing agents, in which the formation of carbon monoxide is minimized and the emission of halogenomethane compounds, in particular of tri- and tetrahalogenomethanes, is prevented.

Alkaline oxidation of organic compounds using hypohalites, preferably sodium hypochlorite, as oxidizing agents is an oxidation process which is often used in practice. This oxidation process is used both for preparative synthesis of organic compounds and, for example in the field of organic pigments and vat dyestuffs, for purification of compounds by destroying impurities and by-products which are unstable under these oxidation conditions by oxidation.

A known preparative oxidation process is the so-called haloform reaction, in which compounds of the type (1) or (2), in which R is an organic radical, are subjected to alkaline hypohalite oxidation:

$R-CO-CH_3$ (1)

$R-CO-CH_2-CO-R$ (2)

In this reaction, the CH-acid methyl or methylene group is first halogenated. Hydrolytic cleavage then takes place, in which, in addition to the particular carboxylic acids, halogenomethane compounds, in particular those of the type $CX_4$ and $CHX_3$, and smaller amounts also of halogenated ethylene compounds of the type $C_2X_4$, for example tetrachloroethylene, in which X is chlorine, bromine or a combination thereof, are also formed. The preparation of naphthalene-1,4,5,8-tetracarboxylic acid and its tetraalkali metal salts by aqueous-alkaline hypochlorite oxidation of 2,7-dibromo-1,2,3,6,7,8-hexahydropyrene-1,3,6,8-tetrone (3), which also exists in the tautomeric forms (3*a*) and (3*b*), is an industrially important process.

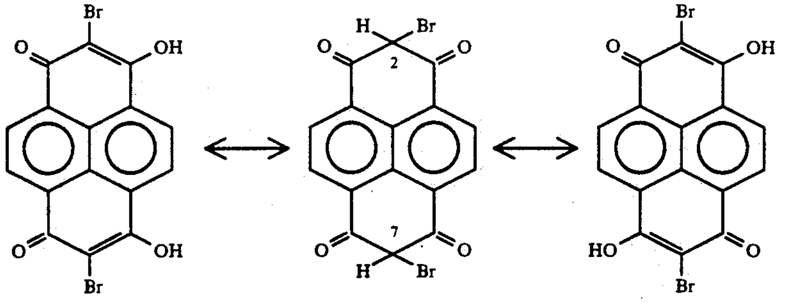

(3a) (3) (3b)

In the aqueous-alkaline hypochlorite oxidation of 2,7-dibromo-1,2,3,6,7,8-hexahydropyrene-1,3,6,8-tetrone (called 2,7-dibromodiindanedione below), according to equation (I), 2 mol of the haloform compound $CHX_3$, in which X is chlorine, bromine or a combination thereof, are formed per mole of the tetraalkali metal salt of naphthalene-1,4,5,8-tetracarboxylic acid.

Equation (I):

-continued

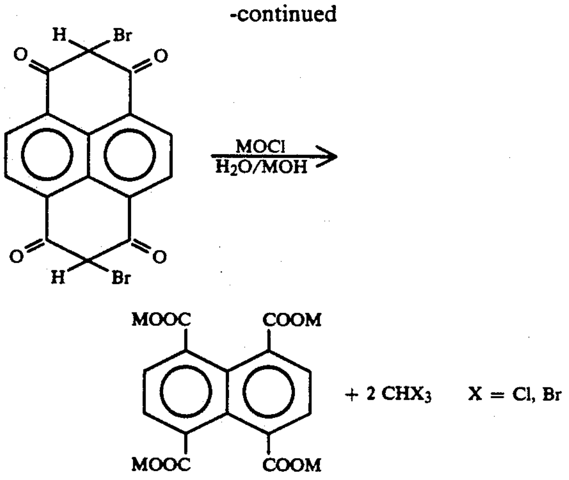

In addition, a small amount of tetrahalogenated compounds of the type $CX_4$, in which X is likewise chlorine, bromine or a combination thereof, occur.

The following halogen-containing compounds can be detected by gas analysis of the reaction products: $CHCl_3$, $CHBrCl_2$, $CHBr_2Cl$, $CHBr_3$, $CCl_4$, $CBrCl_3$, $CBr_2Cl_2$, $CBr_3Cl$ and $CBr_4$. The The haloform compounds $CHX_3$ formed in the oxidation decompose in the course of the hypochlorite oxidation, which is always carried out in an alkaline medium, for example in sodium hydroxide solution or potassium hydroxide solution, at a temperature of about 50° C., predominantly in accordance with equation (II) to give carbon monoxide and alkali metal halide. Hydrolytic decomposition to formate according to equation (III) takes place to only a small extent.

$$CHX_3+3MOH \rightarrow CO+2H_2O+3MX \quad (II)$$

$$CHX_3+4MOH \rightarrow HCOOM+2H_2O+3MX \quad (III)$$

M=Na, K

The carbon monoxide which escapes during the decomposition according to equation (II) represents undesirable pollution of the waste air. However, the fact that the carbon monoxide which escapes during the oxidation entrains compounds of the compound classes $CHX_3$ and $CX_4$ in particular the readily volatile compounds $CHCl_3$ and $CCl_4$, presents considerably greater problems. The removal of these compounds from the waste air, however, requires very great industrial effort. The compounds of the type $CX_4$, which cannot be degraded by alkali under the reaction conditions customary to date, present particular problems.

The object of the present invention is thus to develop a process for the complete hydrolytic decomposition of halogen-containing compounds having one or two carbon atoms and at least 3 halogen atoms per molecule, or mixtures of these compounds, in which halogen is chlorine, bromine or a combination thereof, in particular halogen-containing compounds of the formulae $CHX_3$ and $CX_4$, and of mixtures of these compounds, in which X is chlorine and/or bromine, wherein the emission of the halogen-containing compounds mentioned is minimized as a consequence of this decomposition.

Another object is to employ the process for the complete decomposition of the halogen-containing compounds mentioned in industrially relevant processes in which these halogen-containing compounds are formed in a relatively large amount, for example in the aqueous-alkaline hypohalite oxidation of organic compounds.

It has now been found that the object described can be achieved, surprisingly, by first keeping the aqueous-alkaline reaction mixture comprising the halogen-containing compounds mentioned at a temperature of between 0° and 1000° C. under the autogenous pressure formed therein in a closed reaction vessel for a period of up to 10 hours, preferably 2 to 6 hours, and subsequently subjecting the mixture to a heat treatment at a temperature of between 70° and 150° C. under the autogenous pressure formed therein, in the presence of sulfite.

In a preferred embodiment of the process according to the invention, the halogen-containing compounds $CX_4$ and $CHX_3$ mentioned are reaction products of an aqueous-alkaline hypohalite oxidation of organic compounds.

In another preferred embodiment, the hypohalite oxidation is carried out in a closed reaction vessel at a temperature of 20° to 60° C. under the autogenous pressure formed therein, usually 1 to 5, preferably 1 to 3 bar.

Organic compounds which are employed are preferably those compounds which can be oxidized by aqueous-alkaline hypohalite oxidation to give vat dyestuffs or organic pigments.

The process according to the invention is particularly suitable for the alkali metal hypochlorite oxidation of 2,7-dibromo-1,2,3,6,7,8-hexahydropyrene-1,3,6,8-tetrone to give the tetrasodium salt of naphthalene-1,4,5,8-tetracarboxylic acid.

In the aqueous-alkaline hypohalite oxidation of organic compounds, in particular in the alkaline hypochlorite oxidation of 2,7-dibromodiindanedione (3) to give the tetraalkali metal salt of naphthalene-1,4,5,8-tetracarboxylic acid, the ecological pollution by halogen-containing compounds of the classes $CHX_3$ and $CX_4$, in which X is chlorine, bromine or a combination thereof, is eliminated by carrying out the aqueous-alkaline hypohalite oxidation at a temperature of between 20° and 60° C., preferably 40° to 55° C., in a closed vessel under the autogenous pressure which is established at the corresponding temperature, subjecting the reaction mixture, after the oxidation has ended, to a heat treatment at a temperature of between 90° and 120° C., preferably 90° to 100° C., under the autogenous pressure of 1 to 10 bar, preferably 1 to 5 bar, which is established, in the presence of sulfite, cooling the resulting suspension of the tetrasodium salt of naphthalene-1,4,5,8-tetracarboxylic acid, after the reaction vessel has been let down, to a temperature of below 40° C., preferably to 20° to 30° C., subsequently adjusting the pH to 4.5 to 5 by acidification, isolating the resulting disodium salt of naphthalene-1,4,5,8-tetracarboxylic acid, converting this salt into the tetrasodium salt of naphthalene-1,4,5,8-tetracarboxylic acid in an aqueous alkali metal hydroxide solution and, if appropriate after removal of insoluble impurities, precipitating naphthalene-1,4,5,8-tetracarboxylic acid 1,8-monoanhydride by acidification to a pH of less than 2, preferably less than 1, at a temperature of 80° to 100° C.

The sulfite is added when the oxidation has ended, i.e. when no further hypochlorite is consumed, which is, as a rule, the case after a few hours. It is of advantage here to employ the amount of sulfite in excess, based on the amount of halogen-containing compounds $CX_4$ and $CHX_3$. It is appropriate here to use up to a three-fold, preferably up to a two-fold, molar excess of sulfite. However, less than the equimolar amount of sulfite already causes hydrolytic decomposition of the halogen-containing compounds mentioned. It is not necessary to limit the time of the heat treatment in the presence of sulfite. For economic reasons, it is advantageously carried out over a period of 1 to not more than 20 hours, preferably 3 to 8 hours. The pressure which exists in the reaction vessel at the end of the sulfite treatment is usually 2 to 5 bar.

Suitable alkalies for the alkaline hypohalite oxidation are, above all, sodium hydroxide solution and potassium hydroxide solution. Sodium hydroxide solution is preferred for economic reasons. The alkali is employed in an amount such that, after the oxidation and after the treatment at temperatures of 70° to 150° C. in the presence of sulfite, at least a small excess of alkali is still present. The concentration of the alkali employed is usually between 30 and 50% by weight, and in the case of sodium hydroxide solution is preferably 33% by weight. The amount of alkali can be either added all at once at the start of the oxidation or metered in under pressure in the course of the oxidation.

Hypohalites which are employed are the commercially available alkali metal and alkaline earth metal hypochlorites and hypobromites, although the chlorine bleaching liquor obtainable by passing chlorine into sodium hydroxide solution at a low temperature, preferably below 20° C., is preferably used. If a relatively large amount of hypohalite is employed and the oxidation is carried out at a higher temperature, it is appropriate to meter in the hypohalite in the course of the oxidation, in accordance with its consumption. A preferred embodiment comprises continuously metering in chlorine bleaching liquor to carry out the oxidation, and appropriately keeping the pH in the range from 11 to 12 by simultaneously metering in sodium hydroxide solution. The oxidation is in general carried out at temperatures from 0° to 100° C. Temperatures above 100° C. are also suitable, but are not appropriate because of the extremely rapid decomposition of the hypohalite with disproportionation into halate and halide. At temperatures below 20° C., the oxidation as a rule proceeds very slowly. Oxidation temperatures of 20° to 60° C. are preferred. In this temperature range, the oxidation proceeds sufficiently rapidly and the disproportionation takes place only relatively slowly.

When the oxidation has ended, the excess hypohalite and the halate formed by disproportionation are destroyed reductively by addition of sulfite. The commercially available alkali metal and alkaline earth metal sulfites can be used as the sulfite. Sodium sulfite is preferred. Since the reduction is carried out in an alkaline medium, hydrogen sulfites can also be employed instead of sulfites. The commercially available, approximately 40% strength by weight aqueous sodium hydrogen sulfite solution is preferably used here.

Although the trihalogeno compounds of the type $CHX_3$ formed in the course of the oxidation are already mostly destroyed by hydrolysis during the alkaline oxidation and the subsequent heat treatment at 70° to 150° C. in an alkaline medium, quantitative destruction of these compounds takes place according to the invention only on addition of sulfite. The addition of sulfite is absolutely essential for hydrolytic decomposition of the tetrahalogeno compounds of the type $CX_4$ also formed. Without addition of sulfite, the compounds of the type $CX_4$ are attacked hardly at all in the context of the heat treatment at 70° to 150° C., while in the presence of sulfite the alkaline hydrolysis proceeds virtually completely even under atmospheric pressure. The compounds of the type $CX_4$ are mainly degraded here to carbonates and halides.

The amount of sulfite employed can vary within a wide range, but at least an equimolar amount of sulfite, based on the compounds of the type $CX_4$, and preferably a two-to three-fold excess of sulfite, should appropriately be employed.

The practically complete elimination of compounds of the class $CX_4$ by hydrolytic degradation requires treatment at temperatures of 70° to 150° C. for several hours, preferably 3 to 5 hours. The operation is preferably carried out at temperatures above 90° C. in order to accelerate the decomposition. Temperatures of more than 150° C. are inappropriate in respect of the increased boiler pressures resulting from the temperature. Temperatures of 90° to 120° C., in particular 90° to 100° C., are therefore preferred.

While the compounds of the type $CHX_3$ are decomposed hydrolytically to the extent of about 80% according to equation (II), carbon monoxide being split off, and decomposition according to equation (III) takes place to the extent of only about 20% when the alkaline hypohalite oxidation is carried out under normal pressure in an open reaction vessel, only about 20% of the compounds of the type $CHX_3$ is decomposed according to equation (II), while about 80% is decomposed according to equation (III), when the oxidation is carried out according to the invention in a closed reaction vessel under the autogenous pressure formed therein. Consequently only about 25% of the amount of carbon monoxide formed by oxidation under normal pressure is formed in the process according to the invention.

The waste gas which escapes when the reaction mixture is let down after the after-treatment by heat contains only traces of compounds of the type $CHX_3$, $CX_4$ and $C_2X_4$. These traces can be removed by adsorptive or absorptive after-treatment of the waste gas.

In the case of adsorptive after-treatment, the gas which escapes when the reaction vessel is let down is passed through a vessel filled with a suitable adsorbent. Active charcoal is preferably employed as the adsorbent. In the case of absorptive after-treatment, the waste gas which escapes when the vessel is let down is passed through a vessel filled with a suitable absorption liquid. Examples of suitable absorption liquids are glycol, diethylene glycol, diethylene glycol monoalkyl ethers, glycerol monoalkyl ethers and glycerol bisalkyl ethers, alkyl being understood as meaning $C_1$–$C_4$-alkyl. The absorption is preferably carried out at the lowest possible temperature.

The ecological benefit of the process according to the invention was not predictable, since it was to be assumed that the hydrolytic decomposition of the compound class $CHX_3$ would still proceed mainly in accordance with equation (II) even when the oxidation is carried out under the pressures used of up to 10 bar. Only under pressures of more than 100 bar was it to have been expected that the hydrolytic decomposition would proceed mainly in accordance with equation (III). The high pressures which arise here would have rendered industrial realization of the process uneconomical because of the high costs of such pressure vessels. It was furthermore not to be expected that the compounds of the type $CX_4$ are degraded hydrolytically in an alkaline-aqueous medium in the presence of sulfite at the temperatures used.

The process according to the invention can be used generally for hydrolytic decomposition of compounds of the types $CHX_3$ and $CX_4$ in an aqueous-alkaline medium. It can moreover be used in the case of reactions in which compounds of the types $CHX_3$ and/or $CX_4$ are formed, in which X is chlorine, bromine or a combination thereof, in particular in the case of all alkaline hypohalite oxidations.

With the process according to the invention, pollution of waste air, waste water or clarification residue by compounds of the compound classes $CHX_3$ or $CX_4$ no longer occurs. The process according to the invention is thus an important ecological advance.

In the following examples, parts denote parts by weight and percentages denote percentages by weight.

EXAMPLES

1) Model Experiment

Hydrolytic decomposition of chloroform in aqueous alkali under increased pressure and under atmospheric pressure.

The following two equations apply to the hydrolytic decomposition:

Equation 1: $HCCl_3+3NAOH \rightarrow CO+3NaCl+2H_2O$

Equation 2: $HCCl_3+4NAOH \rightarrow HCOONa+3NaCl+2H2O$ a) Decomposition of Chloroform Under Increased Pressure

A solution of 50 g of sodium hydroxide in 1400 g of water was introduced into a two liter autoclave. The autoclave was then closed. 29.9 g (0.25 mol) of chloroform were then allowed to run in via a pressure lock at a temperature of 20° to 30° C.. The mixture was then stirred at a temperature of 55° to 60° C. for one hour and subsequently at 95° to 100° C. for 3 hours. After the mixture had been cooled to a temperature of 20° to 30° C., an increased pressure of 2 bar prevailed. Since about 5.5 liters of CO would have been formed in the case of complete decomposition of the chloroform in accordance with equation 1, in this case an increased pressure of 10 to 11 bar would have had to occur with a free gas volume of about 0.5 l. When the autoclave was let down and emptied, chloroform was no longer present. Titration of the alkaline reaction solution showed that 37.8 g of sodium hydroxide, corresponding to 0.95 mol, were consumed during the decomposition of chloroform.

Since only 0.75 mol of sodium hydroxide would have been consumed on decomposition of the 0.25 mol of chloroform in accordance with equation 1 and 1 mol of sodium hydroxide would have been consumed in accordance with equation 2, the actual consumption of 0.95 mol of sodium hydroxide demonstrates that in the case of decomposition of chloroform under pressure, 80% of the chloroform was decomposed in accordance with equation 2 and only 20% in accordance with equation 1. This can also be seen from the autoclave pressure which occurs.

b) Decomposition of Chloroform Under Atmospheric Pressure

A solution of 200 g of sodium hydroxide in 1250 g of water was initially introduced into a reaction flask which was provided with a very long intensive condenser, to largely avoid losses of chloroform, and with a water-filled gas wash bottle downstream, to observe the evolution of gas. 119.5 g (1 mol) of chloroform were then allowed to run in at a temperature of 20° to 30° C. The mixture was heated to a temperature of 55° C., while stirring constantly, and was stirred at 55° to 60° C. for 3 hours. As was observed from the water-filled gas wash bottle and as was confirmed by gas analysis, a very vigorous evolution of carbon monoxide gas first started, which proceeded violently in the first half hour and then became weaker. The reaction mixture was then kept at a temperature of 95° to 100° C. for a further hour. After this time, the chloroform had decomposed completely.

Titration of the alkaline reaction solution which remained showed that 131.4 g of sodium hydroxide, corresponding to 3.29 mol, were consumed. Since 3 mol of sodium hydroxide would have had to have been consumed in the case of chloroform decomposition in accordance with equation 1 and 4 mol of sodium hydroxide would have had to have been consumed in accordance with equation 2, the actual consumption of 3.29 mol of sodium hydroxide shows that during decomposition under normal pressure, only 29% of the chloroform was decomposed in accordance with equation 2, but 71% was decomposed in accordance with equation 1.

In contrast to the decomposition in an autoclave under the autogenous pressure formed therein, the decomposition under atmospheric pressure takes place mainly in accordance with equation 1, i.e. with liberation of carbon monoxide.

c) The compounds $CHBrCl_2$, $CHBr_2Cl$ and $CHBr_3$ were decomposed analogously by alkali conditions on the one hand under atmospheric pressure and on the other hand under the autogenous pressure established in the autoclave. Almost the same decomposition ratios occurred here as in the case of chloroform.

2) Model Experiment

Decomposition of Carbon Tetrachloride a) 600 g of a 10% strength aqueous sodium hydroxide solution and 100 g of a 40% strength aqueous sodium hydrogen sulfite solution were initially introduced into a stirred apparatus with a long intensive condenser. 30.8 g (0.2 mol) of carbon tetrachloride were then allowed to run in at a temperature of 20° to 30° C., while stirring constantly. The mixture was then heated slowly to the boiling point, and heated under reflux for 4 hours. After cooling to about 25° C., the organic layer had disappeared completely, i.e. the carbon tetrachloride was decomposed hydrolytically.

b) Comparison Example 600 g of a 10% strength aqueous sodium hydroxide solution were initially introduced into a stirred apparatus with a long intensive condenser. 30.8 g (0.2 mol) of carbon tetrachloride were then allowed to run in at a temperature of 20° to 30° C., while stirring constantly. The mixture was then heated to the boiling point, and heated under reflux for a further 4 hours. After cooling to room temperature, the organic layer was still completely present. It was possible to recover the carbon tetrachloride in unchanged form by steam distillation. Titration of the aqueous alkali showed that no sodium hydroxide had been consumed.

EXAMPLE 3 a) A solution of 90 g of sodium hydroxide in 650 g of water was initially introduced into a two liter autoclave. 115 g (about 0.18 mol) of industrial 2,7-dibromodiindanedione having a purity of 66% were then added, while stirring. The autoclave was then closed. 800 g of industrial chlorine bleaching liquor (prepared by passing chlorine into sodium hydroxide solution at a temperature of 20° to 30° C., active chlorine content: about 12%) was then allowed to run in slowly via a pressure lock, the temperature being allowed to rise slowly, with gentle cooling, to 40° to 50° C. After the end of the addition of the bleaching liquor, the mixture was subsequently stirred at a temperature of 50° to 55° C. for a further 4 hours. A hypochlorite excess was present throughout the entire after-stirring time. The increased pressure at the end of the after-stirring time of four hours was 2 to 3 bar.

A gas sample was taken in the course of and toward the end of the addition of the chlorine bleaching liquor and then analysed. The following compounds of the class $CHX_3$ were detected: $CHCl_3$, $CHBrCl_2$, $CHBr_2Cl$ and $CHBr_3$, the compound $CHBrCl_2$ being present as the main component. In addition, compounds of the general formula $CX_4$, that is to say $CCl_4$, $CBrCl_3$, $CBr_2Cl_2$, $CBr_3Cl$ and $CBr_4$, were also present in smaller amounts.

b) 90 g of a 40% strength aqueous sodium hydrogen sulfite solution were then allowed to run in via a pressure lock at a temperature of 50° to 55° C. and the mixture was stirred at 90° to 100° C. for a further 3 hours. It was then cooled to 20° to 30° C. An increased pressure of about 3 bar prevailed. The increased pressure was then let down very slowly. The gas which came off was passed through an adsorber vessel filled with active charcoal. The gas leaving the adsorber vessel consisted to the extent of about 50% of carbon monoxide. The gas was free from halogenohydrocarbons.

c) The suspension, present after the letting down, of the tetrasodium salt of naphthalene-1,4,5,8-tetracarboxylic acid (called NTC below) was brought to a pH of 4.8–4.5 with about 150 g of a 31% strength hydrochloric acid at a temperature of 20° to 30° C. The mixture was subsequently stirred at 20° to 30° C. and pH 4.8 to 4.5 for 3 hours, until the disodium salt of NTC, which is sparingly soluble in water, had formed. The solid was then rapidly filtered off with suction. The filter cake was introduced into 1500 g of water. The mixture was heated to a temperature of 70° to 80° C., and a pH of 10 to 10.5 was established at this temperature by slow addition of about 46 g of a 33% strength aqueous sodium hydroxide solution. During this operation, the NTC dissolved as the tetrasodium salt. After addition of about 5 g of active charcoal and about 5 g of kieselguhr, the solid was filtered off hot, with suction, and rinsed with a little water. The clear filtrate was heated to 80° to 100° C. A pH of 0.5 to 1 was then established at 80° to 100° C. by slow addition of about 130 g of a 31% strength hydrochloric acid. The mixture was subsequently stirred at 80° to 100° C. for one hour. The coarsely crystalline product which had precipitated was then filtered off with suction and the filter cake was washed with about 500 g of a 1% strength hydrochloric acid. The product was dried at 100° C. 52 g of naphthalene-1,4,5,8-tetracarboxylic acid 1,8-monoanhydride of 96% purity, corresponding to a yield of 97% of theory, were obtained. The waste water obtained during the filtration was free from halogenohydrocarbons.

d) Instead of the oxidation being brought to completion at 50° to 55° C., as carried out under a), the oxidation was advantageously carried out first at 50° to 55° C. for 2 hours and then at 65° to 70° C. for a further 2 hours. The increased pressure at the end of the oxidation was about 3 bar.

e) Instead of the alkaline decomposition of the residual halogenohydrocarbons at 90° to 100° C. carried out under b) after addition of the sodium hydrogen sulfite solution, this decomposition was carried out at 110° to 120° C. for 5 hours. After cooling to 20° to 30° C., an increased pressure of about 3 bar prevailed.

f) Instead of using chlorine bleaching liquor, the oxidation according to a) was carried out with a sodium hypochlorite solution which was free from sodium chloride and had the same active chlorine content, and with a potassium hypochlorite solution, the same result as described under c) being achieved.

g) Instead of the adsorptive after-treatment of the gas with active charcoal carried out under b), the gas was passed through an absorber vessel filled with diethylene glycol monomethyl ether and cooled to a temperature of −10° C. In this case also, the residual halogenohydrocarbons were removed from the waste gas.

4) Comparison Example

Oxidation of 2,7-Dibromodiindanedione Under Atmospheric Pressure

The oxidation of 2,7-dibromodiindanedione according to Example 3 a) was carried out in an analogous manner, but under atmospheric pressure. Very vigorous evolution of gas occurred during the addition of chlorine bleaching liquor, this evolution constantly entraining some of the halogenohydrocarbons formed, i.e. $CHCl_3$, $CHBrCl_2$, $CHBr_2Cl$, $CHBr_3$, $CCl_4$, $CBrCl_3$, $CBr_2Cl_2$, $CBr_3Cl$ and $CBr_4$. Because of the very vigorous stream of gas, the halogenohydrocarbons could not be bonded completely by adsorption or absorption on an industrial scale, and escaped into the environment.

EXAMPLE 5 a) 147 kg of water and 104 kg of a 33% strength sodium hydroxide solution were initially introduced into a 700 liter boiler. 31.6 kg of 2,7-dibromodiindanedione of about 61% purity (corresponding to about 45.7 mol) were then introduced, while stirring. The boiler was then closed. 300 kg of chlorine bleaching liquor (active chlorine content about 12%) were subsequently allowed to run in under pressure in the course of 2 to 3 hours. An increase in temperature to above 55° C. was prevented by cooling with water during the addition of the bleaching liquor. When the addition had ended, the mixture was subsequently stirred at a temperature of 50° to 55° C. for 2 hours, during which an increased pressure of 2.5 bar occurred. An excess of hypochlorite was present in the reaction mixture throughout the entire after-stirring time.

b) When the oxidation had ended, 30 kg of a 40% strength aqueous sodium hydrogen sulfite solution were metered into the reaction mixture under pressure. Only a small portion of the sulfite present in the system was required for reductive decomposition of the excess hypochlorite. The mixture was then heated to a temperature of 95° C. and stirred at 95° to 105° C. for 3 hours, during which an increased pressure of about 4 bar occurred. After cooling to about 50° C., the boiler was let down slowly and the gas which came off was passed through a vessel filled with active charcoal. The boiler was flushed with a small amount of nitrogen. The gas leaving the adsorber vessel was free from halogenohydrocarbons. The waste gas, which contained about 50% of carbon monoxide, was passed for combustion.

c) After cooling to a temperature of 20° to 30° C., the suspension, which was present after the letting down, of the tetrasodium salt of naphthalene-1,4,5,8-tetracarboxylic acid (NTC) was worked up by a process analogous to that described in Example 3 c), by a procedure in which the disodium salt of NTC was first formed by acidification to pH 4.8 to 4.5 and was isolated, this salt was then dissolved in water by conversion into the tetrasodium salt, insoluble impurities were separated off by filtration, and the 1,8-monoanhydride of NTC was then precipitated by acidification with hydrochloric acid and was isolated. 13.1 kg of naphthalene-1,4,5,8-tetracarboxylic acid 1,8-monoanhydride of 96% purity, corresponding to a yield of 97% of theory, were obtained.

EXAMPLE 6 a) The oxidation of 2,7-dibromodiindanedione was first carried out analogously to Example 5 a). When the oxidation had ended, 30 kg of an aqueous sodium hydrogen sulfite solution were also metered in at 50° to 55° C., but then the after-treatment by heat described in Example 5 b) was dispensed with and the boiler was let down at a temperature of 50° to 55° C. without this after-treatment and without the use of an active charcoal adsorber. The waste gas still contained about 288 g of halogenohydrocarbons, and in particular as main components 205 g of $CHCl_3$, 50 g of $CCl_4$, 4 g of $CHBrCl_2$ and 26 g of $CBrCl_3$.

b) The oxidation of 2,7-dibromodiindanedione and the subsequent decomposition by heat were carried out analogously to Example 5 a) and b). After cooling to 50° C., the waste gas was discharged without using the active charcoal adsorber. This waste gas still contained about 27 g of halogenohydrocarbons, and in particular as main components 7 g of $CHCl_3$ and 19 g of $CCl_4$. Since during the oxidation, calculated exclusively with respect to $CHBrCl_2$, about 15 kg of this compound are formed, the small residue of halogenohydrocarbons demonstrates the effectiveness of the process. Comparison of the pollution of the waste gas with halogenohydrocarbons in Example 6 b) against Example 6 a) also demonstrates the effectiveness of the after-treatment by heat in the presence of excess sulfite.

We claim:

1. A process for the hydrolytic decomposition of a halogen-containing compound of the formula $CX_4$ or $CHX_3$ or a mixture of these compounds, in which X is the halogen chlorine or bromine or a combination thereof, which comprises: subjecting said halogen-containing compound to the hydrolytic decomposition in an aqueous-alkaline mixture at a temperature of between 0° and 100° under the autogenous pressure formed therein in a closed reaction vessel for a period of up to 10 hours and subsequently subjecting the mixture to heat treatment at a temperature of between 70° and 150° C. under the autogenous pressure formed therein, in the presence of sulfite.

2. The process as claimed in claim 1, wherein the halogen-containing compound is a reaction product of an aqueous-alkaline hypohalite oxidation of an organic compound.

3. The process as claimed in claim 2, wherein the alkaline hypohalite oxidation is carried out in a closed reaction vessel at a temperature of 20° to 60° C. under the autogenous pressure formed therein.

4. The process as claimed in claim 3, wherein the alkaline hypohalite oxidation is carried out in a closed reaction vessel at a temperature of 40° to 55° C. under the autogenous pressure formed therein.

5. The process as claimed in claim 2, wherein the organic compound employed is an organic compound which can be oxidized by aqueous-alkaline hypohalite oxidation to give a vat dyestuff or organic pigment.

6. The process as claimed in claim 2, wherein 2,7-dibromo-1,2,3,6,7,8-hexahydropyrene-1,3,6,8-tetrone, as the organic compound, is oxidized in an aqueous-alkaline medium with an alkali metal hypochlorite to give the tetrasodium salt of naphthalene-1,4,5,8-tetracarboxylic acid.

7. The process as claimed in claim 1, wherein the heat treatment of the reaction mixture is carried out in the presence of sulfite at a temperature of 90° to 120° C. under the autogenous pressure which is formed therein.

8. The process is claimed in claim 1, wherein the heat treatment of the reaction mixture is carried out in the presence of sulfite at a temperature of 90° to 100° C. under the autogenous pressure which is formed therein.

9. The process as claimed in claim 6, wherein, after the oxidation has ended the reaction mixture is subjected to a heat treatment at a temperature of between 90° and 120° C. under the autogenous pressure of 1 to 10 bar which is established, in the presence of sulfite, the resulting suspension of the tetrasodium salt of naphthalene-1,4,5,8-tetracarboxylic acid is cooled, after the reaction vessel has been let down, to a temperature of below 40° C. the pH is then adjusted to 4.5 to 5 by acidification, the resulting disodium salt of naphthalene-1,4,5,8-tetracarboxylic acid is isolated, this salt is converted into the tetrasodium salt of naphthalene-1,4,5,8-tetracarboxylic acid in an aqueous alkali metal hydroxide solution and, optionally after removal of insoluble impurities, naphthalene-1,4,5,8-tetracarboxylic acid 1,8-monoanhydride is precipitated by acidification to a pH of less than 2 at a temperature of 80° to 100° C.

10. The process as claimed in claim 9, wherein, after the oxidation has ended, the reaction mixture is subjected to a heat treatment at a temperature of between 90° and 100° C. under the autogenous pressure of 1 to 5 bar which is established, in the presence of sulfite, the resulting suspension of the tetrasodium salt of naphthalene-1,4,5,8-tetracarboxylic acid is cooled, after the reaction vessel has been let down, to a temperature of 20° to 30° C. the pH is then adjusted to 4.5 to 5 by acidification, the resulting disodium salt of naphthalene-1,4,5,8-tetracarboxylic acid is isolated, this salt is converted into the tetrasodium salt of naphthalene-1,4,5,8-tetracarboxylic acid in an aqueous alkali metal hydroxide solution and, optionally after removal of insoluble impurities, naphthalene-1,4,5,8-tetracarboxylic acid 1,8-monoanhydride is precipitated by acidification to a pH of less than 1 at a temperature of 80° to 100° C.

11. The process as claimed in claim 2, wherein the hypohalite oxidation is carried out with an alkali metal hypochlorite or an alkali metal hypobromite or a mixture thereof.

12. The process as claimed in claim 11, wherein the alkali metal hypochlorite is sodium hypochlorite.

13. The process as claimed in claim 1, wherein an alkali metal sulfite, an alkaline earth metal sulfite, an alkali metal hydrogen sulfite or a mixture of these sulfites is employed as the sulfite.

14. The process as claimed in claim 1, wherein sodium sulfite is employed as the sulfite.

15. The process as claimed in claim 1, wherein an aqueous sodium hydrogen sulfite solution is employed as the sulfite.

16. The process as claimed in claim 1, wherein the amount of sulfite is present in up to a three-fold excess, based on the total amount of halogen-containing compounds $CHX_3$ and $CX_4$.

17. The process as claimed in claim 16, wherein the amount of sulfite is present in up to a two-fold excess, based on the total amount of halogen-containing compounds $CHX_3$ and $CX_4$.

18. The process as claimed in claim 1, wherein, after the heat treatment in the presence of sulfite has been completed, and a waste gas is present in the reaction vessel, the resulting reaction mixture is cooled to a temperature of less than 100° C., the reaction vessel is then opened and the waste gas is led away from the opened reaction vessel to an adsorptive or absorptive after-treatment zone.

19. The process as claimed in claim 21, wherein the adsorptive after-treatment of the waste gas is carried out with active charcoal.

20. The process as claimed in claim 18, wherein the absorptive after-treatment of the waste gas is carried out using glycol monoalkyl ether, a glycerol monoalkyl ether or a glycerol dialkyl ether as the absorbent at the lowest possible temperature at which said absorptive after-treatment is effective.

* * * * *